United States Patent
Hellstrom (10) Patent No.: US 7,593,106 B2
(45) Date of Patent: Sep. 22, 2009

(54) INDEPENDENT MEASUREMENT OF DUAL SIDED PROPERTIES OF SHEET MATERIAL

(75) Inventor: Ake Arvid Hellstrom, Columbus, OH (US)

(73) Assignee: ABB Ltd., Dublin (IE)

( * ) Notice: Subject to any disclaimer, the term of this patent is extended or adjusted under 35 U.S.C. 154(b) by 406 days.

(21) Appl. No.: 11/439,653

(22) Filed: May 24, 2006

(65) Prior Publication Data
US 2007/0295077 A1 Dec. 27, 2007

(51) Int. Cl.
G01N 21/84 (2006.01)
(52) U.S. Cl. .......................... 356/430; 356/429; 356/435
(58) Field of Classification Search .................. None
See application file for complete search history.

(56) References Cited

U.S. PATENT DOCUMENTS

| | | | | |
|---|---|---|---|---|
| 4,714,340 A | * | 12/1987 | Stillwagon | 356/430 |
| 4,937,449 A | | 6/1990 | Kreuzer et al. | |
| 5,071,514 A | * | 12/1991 | Francis | 356/429 |
| 5,343,296 A | | 8/1994 | Hellstrom | |
| 5,640,244 A | * | 6/1997 | Hellstrom et al. | 356/429 |
| 5,991,046 A | * | 11/1999 | Shakespeare et al. | 356/429 |
| 6,233,053 B1 | | 5/2001 | Preston et al. | |
| 6,242,733 B1 | * | 6/2001 | Ma et al. | 250/223 R |
| 6,588,118 B2 | | 7/2003 | Hellstrom | |
| 7,323,085 B2 | * | 1/2008 | Ischdonat et al. | 356/429 |
| 7,345,772 B2 | * | 3/2008 | Typpo | 356/429 |
| 2002/0011319 A1 | | 1/2002 | Shakespeare et al. | |

FOREIGN PATENT DOCUMENTS

| | | |
|---|---|---|
| EP | 1655881 | 5/2006 |
| WOPCTUS2007011575SR | | 11/2007 |
| WOPCTUS2007011575PR | | 12/2008 |

* cited by examiner

*Primary Examiner*—Michael A Lyons
*Assistant Examiner*—Juan D Valentin
(74) *Attorney, Agent, or Firm*—Michael M. Rickin; Paul R. Katterle (57) ABSTRACT

A dual sided sheet surface property sensor has the capability to simultaneously measure both sides of a moving sheet at the same location of the sheet on the top and bottom surfaces of the sheet. The energy directed to each side of the sheet may include UV, visible light, infrared, radio frequency, microwave, broadband, or X-ray. The sensor has a source and associated detector on each side of the moving sheet and each source provides energy at a different modulation frequency and the associated detector is responsive only to that frequency.

18 Claims, 11 Drawing Sheets

INDEPENDENT MEASUREMENT OF DUAL SIDED PROPERTIES OF SHEET MATERIAL

FIELD OF THE INVENTION

This invention relates to measurement of the top and bottom side quality properties of a material sheet and more particularly to independent measurement of those quality properties.

DESCRIPTION OF THE PRIOR ART

Figure 1:
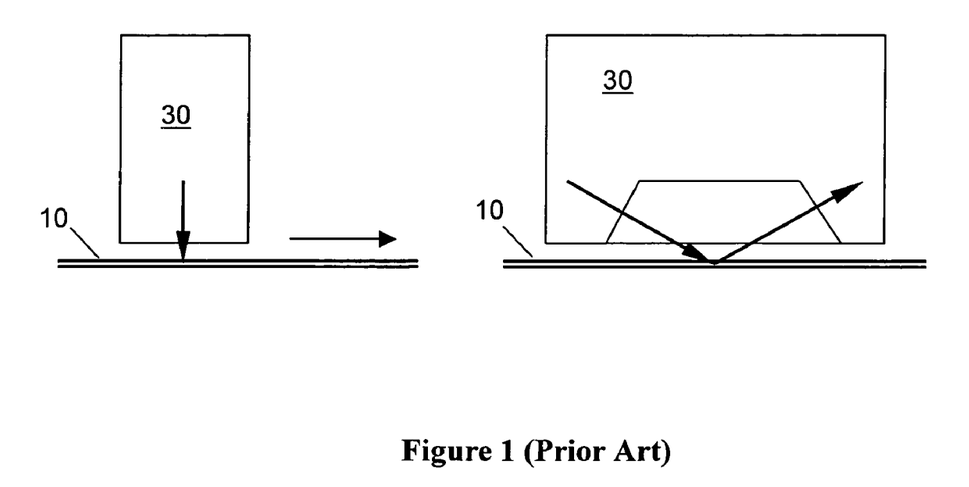
FIG. 1 shows a prior art source and detector on one side of a moving sheet for measuring sheet surface quality parameters in a sheet making or sheet converting process.

Measurement of sheet surface quality parameters in a sheet making or sheet converting process, for example, gloss on both sides of a paper web, may be performed with scanning or non-scanning systems. The measurement system may include an energy source and an energy detector 12 as schematically illustrated in FIG. 1 where 10 is the moving sheet. FIG. 1 illustrates in (a) and (b) side and front views for the energy source and the energy detector 12. As is shown in front view (b) the energy source and the detector 12 are located on the same side of the moving sheet 10.

Figure 2:
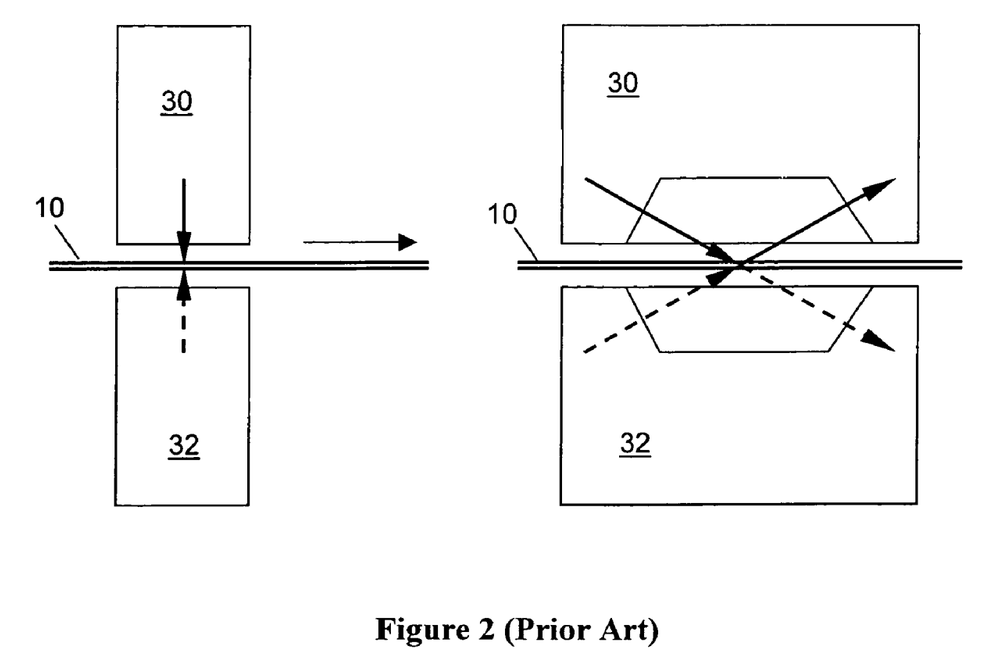
FIG. 2 a prior art source and detector on each side of a moving sheet for measuring sheet surface quality parameters in a sheet making or sheet converting process.

Surface quality is frequently critical for both sides of the sheet. Examples include dual sided gloss on paper. Often, the sheet product is not fully opaque and has some degree of translucency. This makes accurate and independent measurement of dual sided quality difficult due to cross talk from the opposing side measurement energy leaking through the sheet. This is illustrated in FIG. 2 for the same side and front views (a) and (b) shown in FIG. 1 except that instead of a single combination source and detector 12 on one side of the moving sheet 10 there is shown in FIG. 2 a combination source and detector 20a on one side of moving sheet 10 and another combination source and detector 20b on the other side of moving sheet 10. Since the moving sheet 10 has some degree of translucency the signal from the source of combination source and detector 20a may leak through sheet 10 to the detector of combination source and detector 20b making the measurement by that combination of the gloss on the bottom side of sheet 10 inaccurate and vice versa.

Figure 3:
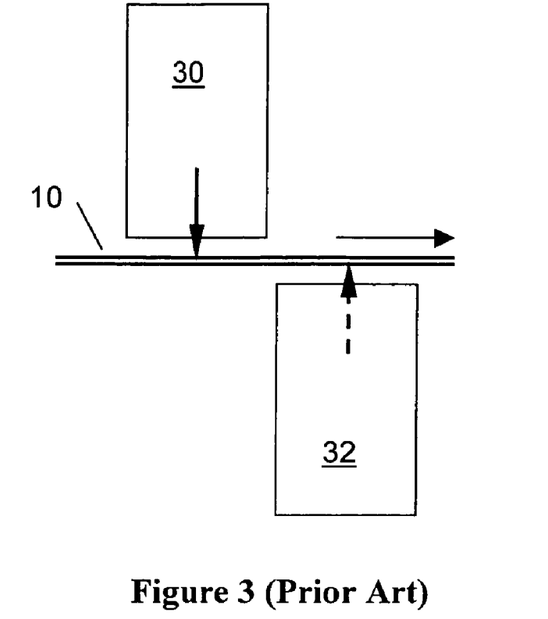
FIG. 3 shows a prior art arrangement of source and detector which are physically separated in the machine direction and FIG. 4 shows such an arrangement in the cross direction.
Figure 4:
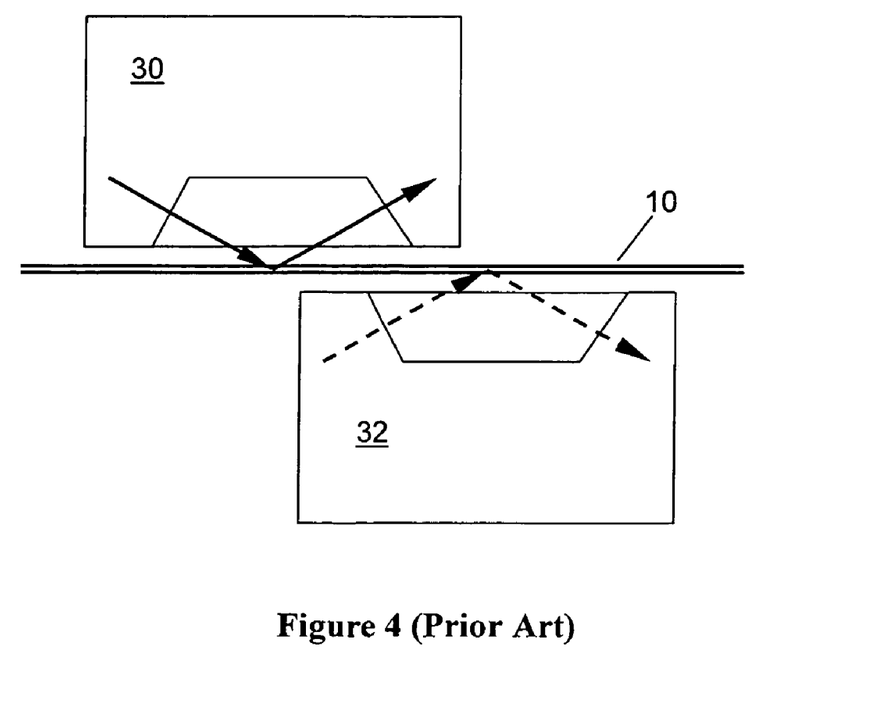

Remedies for cross talk include physical separation of the measurement devices for the top and bottom side in the plane of the sheet. The physical separation may be accomplished by separate measurement locations in the cross machine direction, but in doing so the measurements do not line up in the cross direction to represent the same physical location on each side of the sheet. If the measurement locations are physically separated in the machine direction, the total dimensions of the sensor package will increase. This is an disadvantage that increases cost and limits the number of sensors that can be arranged for a given process. Physically separated measurement of a sensor head pair in the machine direction is illustrated in FIG. 3 and in the cross machine direction is illustrated in FIG. 4. The measurement energy and detection may, in these two cases, be directed or detected from any positional relation to the machine direction or the sheet.

Another remedy for cross talk is to utilize different measurement energy, for instance different wavelengths of light, for top and bottom side measurement of moving sheet 10, and selectively only detect the specific energy type on each side. This has the drawback of making the dual sided measurement react differently for sheet quality parameters on each side of sheet 10.

Yet another method eliminates cross talk by periodically enabling and disabling the energy source for one or the other side of moving sheet 10 in order to temporarily remove the cross talk source from the undesirable side. This causes an interruption for one side of the measurement and requires careful synchronization or timing of the operation between top and bottom sides. Furthermore this method needs complex data handling to estimate or extrapolate values for the lost measurement areas.

Measurement of dual sided properties is sometimes accompanied by a calculation that uses information measured from both sides of the sheet 10. This calculation includes estimation of small scale uniformity of the sheet 10, or measurement of thickness, flatness, waviness or other dimensional properties. These derived measurements will have inaccuracy unless the separate top and bottom side measurements are performed at the same physical sheet location as illustrated in FIG. 2. The machine direction and cross direction offset arrangements shown in FIGS. 3 and 4, respectively, have an disadvantage in this case. It is desired to achieve a compact measurement system by measuring both sides of the sheet at the same location. Examples of the physical arrangement of particularly compact dual sided sensor can be found in U.S. Pat. No. 6,588,118 entitled "Non-Contacting Sheet Sensing And Related Method" the disclosure of which is hereby incorporated herein by reference.

The present invention provides a universal remedy for all of the problems described above with the presently available methods for measurement of dual sided properties of a moving sheet. The method and apparatus of the present invention is adaptable for measurement of several different sheet properties and different energy types utilized in the measurement.

SUMMARY OF THE INVENTION

A method for measuring properties of a moving web in which sensor heads having at least one source for providing energy and at least one associated detector for detecting energy reflected from the web to be measured are installed on both of sides of the web to measure the same location on the web. The method:

provides from the at least one source on one side of the web energy modulated at a first frequency;

simultaneously provides from the at least one source on the other side of the web energy modulated at a second frequency which is different than the first frequency;

the at least one detector on the one side of the web detecting only energy reflected from the web modulated at the first frequency; and the at least one detector on the other side of the web detecting only energy reflected from the web modulated at the second frequency.

An apparatus for measuring properties of a moving web. The apparatus has:

first and second sensor heads for installation on opposite sides of the web to measure the same location on the web, each of the first and second sensor heads comprising at least one source for providing energy and at least one associated detector for detecting energy reflected from the web; and the at least one source of the first sensor head providing energy modulated at the first frequency and the at least one source of the second sensor head providing energy modulated at the second frequency which is different than the first frequency;

the at least one detector of the first sensor head detects only energy reflected from the web modulated at a first frequency and the at least one detector of the second sensor head detects only energy reflected from the web modulated at a second frequency.

A system for measuring properties of a moving web. The system has:

a machine for making the moving web, the machine comprising one or more frames mounted on the machine such that each of the one or more frames straddles the moving web;

one or more quality control systems for controlling one or more properties of the moving web; and one or more sensors mounted on at least one of the one or more frames. Each of the one or more sensors have:

first and second sensor heads mounted on the at least one of the one or more frames such that the heads are on opposite sides of the web to measure the same location on the web, each of the first and second sensor heads comprising at least one source for providing energy and at least one associated detector for detecting energy reflected from the web; and the at least one source of the first sensor head providing energy modulated at the first frequency and the at least one source of the second sensor head providing energy modulated at the second frequency which is different than the first frequency;

the at least one detector of the first sensor head detects only energy reflected from the web modulated at a first frequency and the at least one detector of the second sensor head detects only energy reflected from the web modulated at a second frequency.

DETAILED DESCRIPTION

A dual sided sheet surface property sensor embodied in accordance with the present invention is capable of measuring both sides of a moving sheet at the same location of the sheet on the top and bottom sides of the sheet. The energy directed to each side may include UV, visible light, infrared, radio frequency, microwave, broadband, or X-ray. Applications of the present invention include, but are not limited to, the measurement of several sheet properties including gloss, brightness, smoothness, texture, color, coat weight, crepe, surface moisture and non-contacting caliper. These properties as is well known to those in the art can, depending upon the energy directed to each side of the sheet and type of detectors used, be measured independently of each other or more than one property may be measured at the same time. For example, if the energy source is broadband light both moisture and brightness can be simultaneously measured.

Figure 5:
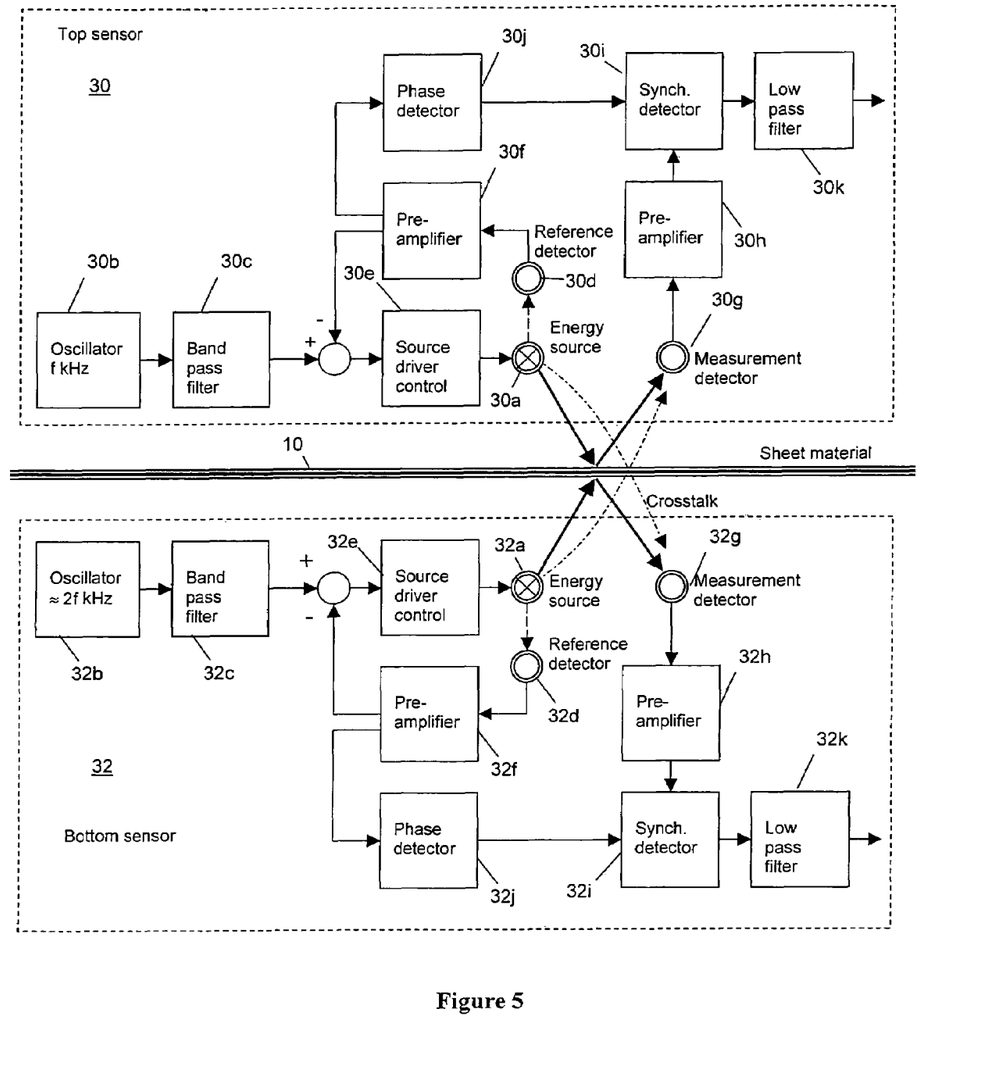
FIG. 5 shows first and second source and detector combinations embodied in accordance with the present invention on opposite sides of a moving sheet.

Referring now to FIG. 5, there is shown moving sheet 10 and first and second combination source and detector sensors 30 and 32 with sensor 30 located on the top side of sheet 10 and sensor 32 located on the bottom side of sheet 10. As illustrated in FIG. 5, the measurement energy in each sensor head is generated by a source, 30a in sensor head 30 and 32a in sensor head 32, on each side of the sheet. This source 30a, 32a in each sensing head is modulated by means of an associated oscillator 30b, 32b, a band pass filter 30c, 32c, a reference detector 30d, 32d and a source driver controller 30e, 32e.

The oscillator 30b, 32b generates a well-defined and repetitive waveform, for instance sinusoidal. The oscillator frequency in one of the heads is preferably approximately two times the frequency of the oscillator in the opposing head. The reason for this choice of frequency ratio is related to achieving best possible sheet property measurement frequency response after demodulation and filtering, lowest possible modulation rate of the sources at a desired process measurement response, and minimum low frequency cross talk that might be caused by mixing between the two oscillator frequencies.

The frequency of oscillator 30b or 32b, that is the modulation frequency, can be selected to allow maximum signal to noise ratio and rejection of aliasing effects due to paper variability. For instance, in a paper machine traveling at 1,200 m/min, a modulation frequency of 20 kHz implies one full modulation cycle per every 1 mm paper travel in the machine direction. This travel distance can be seen in relation to typical sensor measurement apertures in the range of 10 mm in diameter. This means for this example a high degree of oversampling and spatial averaging that greatly reduce modulation aliasing effects from small scale process variability. It also means that no sheet property information from any area of moving sheet 10 is lost as part of the on-sheet measurement cycle.

With a modulation frequency ratio of approximately 2:1 between the two sensor heads, it is important to choose the modulating wave forms with a low level of second harmonic content. If this is not the case, the second harmonic of one sensor modulating frequency may interfere and create a low frequency beat with the primary modulating frequency of the other sensor. A low distortion sine wave has little content of second order harmonics, and so do several other wave forms, for instance symmetrical and exactly 50% duty cycle square waves. In any case, a filter, such as band pass filter 30c, 32c, is preferably inserted after the oscillator 30b, 32b, to further reduce harmonics content. This filter 30c, 32c, causes a roll off of a square wave and create a rounded shape result; however, this is desirable from the view of creating a wave form without excessively fast rise time or fall time, since otherwise the source may not be able to track the desired waveform closely.

A closed loop intensity controller 30e, 32e, is included on each side of moving sheet 10. The controller 30e, 32e, operates by comparing the received energy from an associated reference detector 30d, 32d, and associated pre-amplifier 30f, 32f, with the commanded oscillator wave form using a tight feedback loop and thus forcing the emitted source energy to continuously replicate the modulation waveform.

One or several measurement detectors 30g, 32g is provided in each measurement head, responding to a sheet property measurement from the source energy 30a, 32a on the corresponding side of moving sheet 10. The measurement detector 30g, 32g, is connected via associated preamplifiers 30h, 32h to an associated synchronous detector 30i, 32i. The second input to this detector 30i, 32i, originates from sensing in associated phase detector 30j, 32j zero crossings of the AC signal from reference detector 30d, 32d amplified by associated pre-amplifier 30f, 32f. Choosing a reference detector 30d, 32d, and measurement detector 30g, 32g, of similar characteristics, provides a well balanced and properly phase locked synchronous demodulation at the associated oscillator frequency and with proper compensation for time lags and other non ideal response.

A low pass filter 30k, 32k, is provided at the output of sensor 30, 32, to eliminate modulation frequencies and high frequency cross talk from the opposing side of moving sheet 10. A ratio of approximately 1:10 of low pass filter corner frequency and oscillator frequency allows for a good systems response and low residual noise, while requiring only a $4^{th}$ order low pass filter characteristics.

Figure 6A:
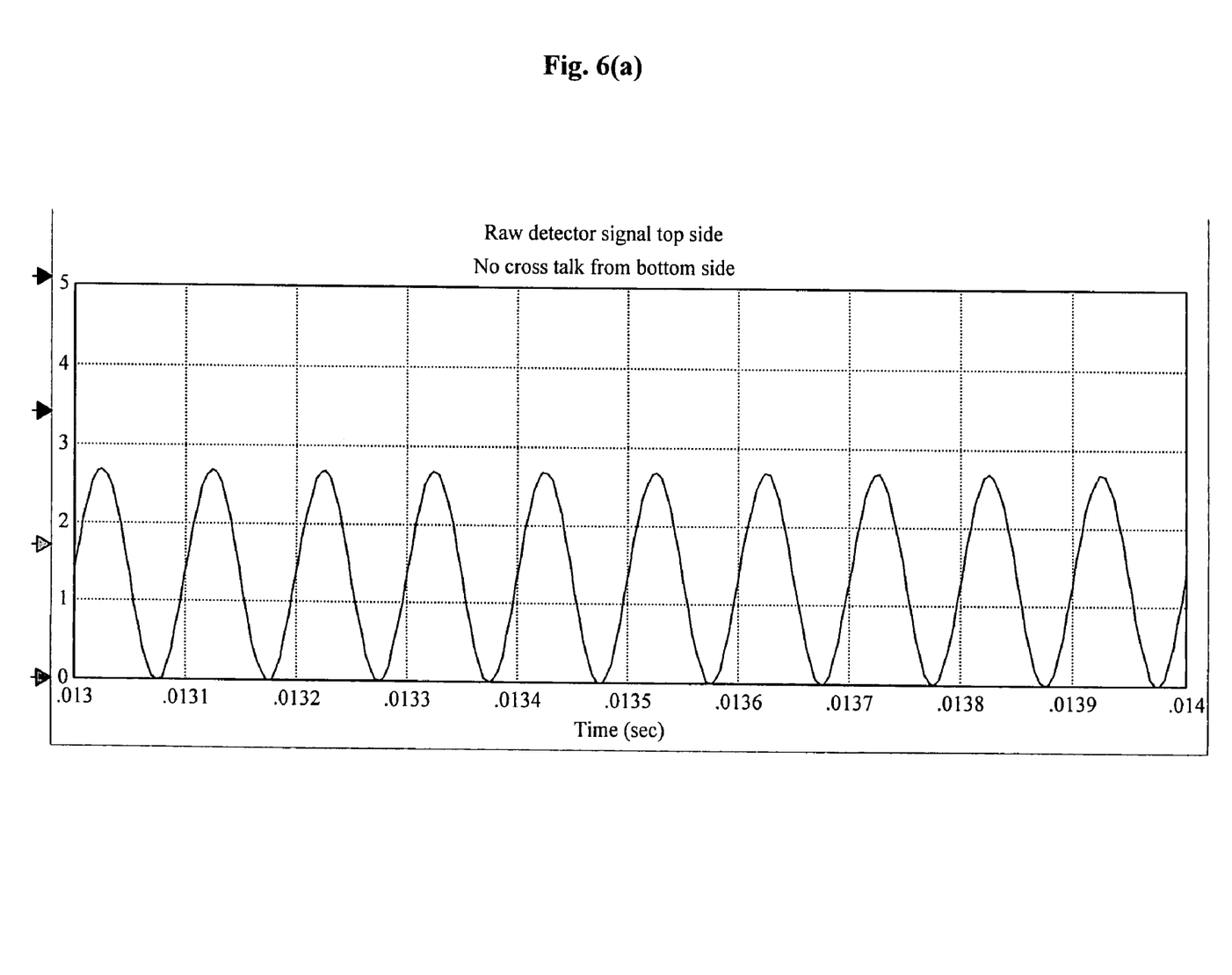
FIGS. 6(a), (b) and (c) show examples of waveforms for the upper and lower sensors of FIG. 5.
Figure 6B:
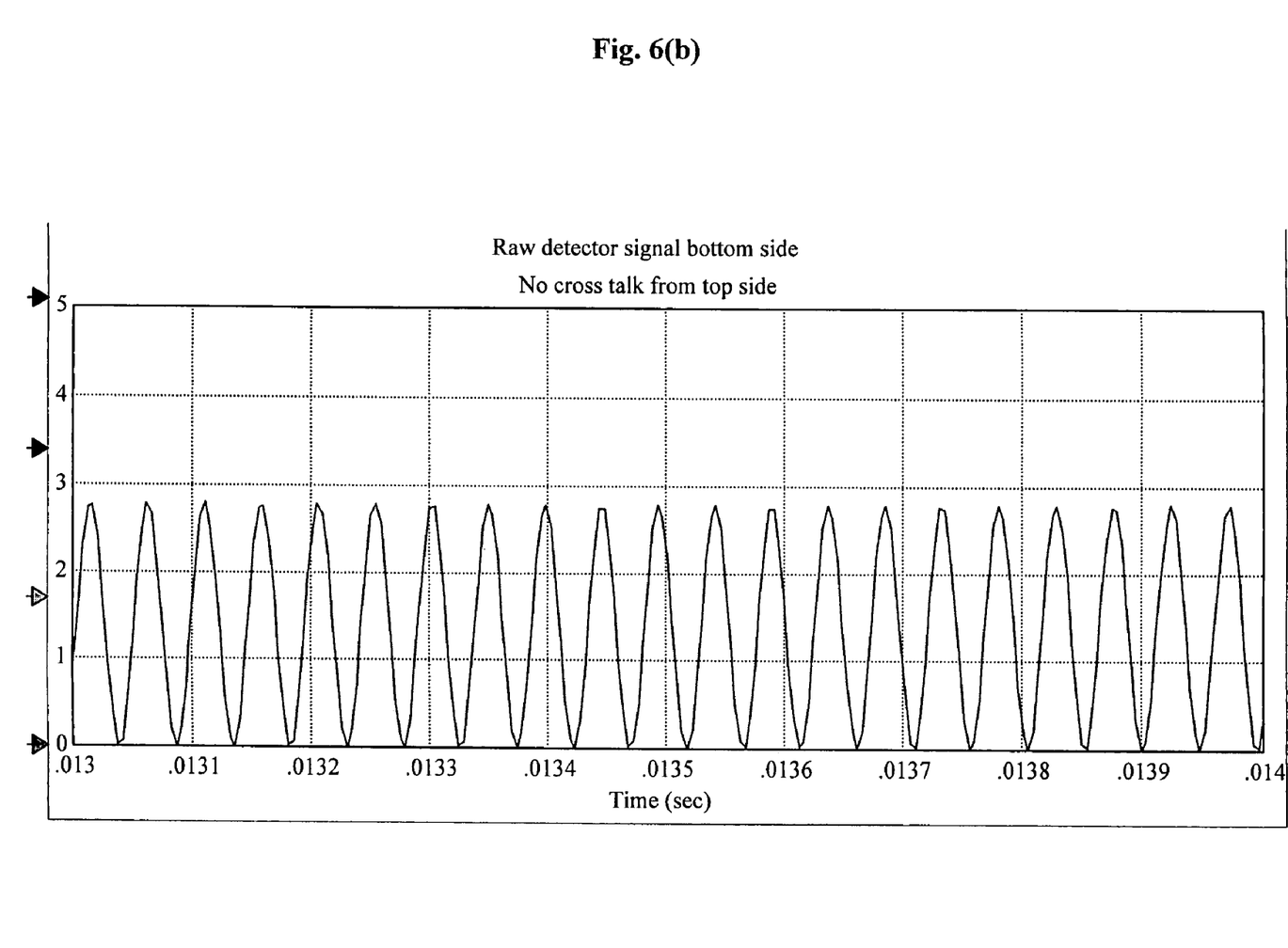
Figure 6C:
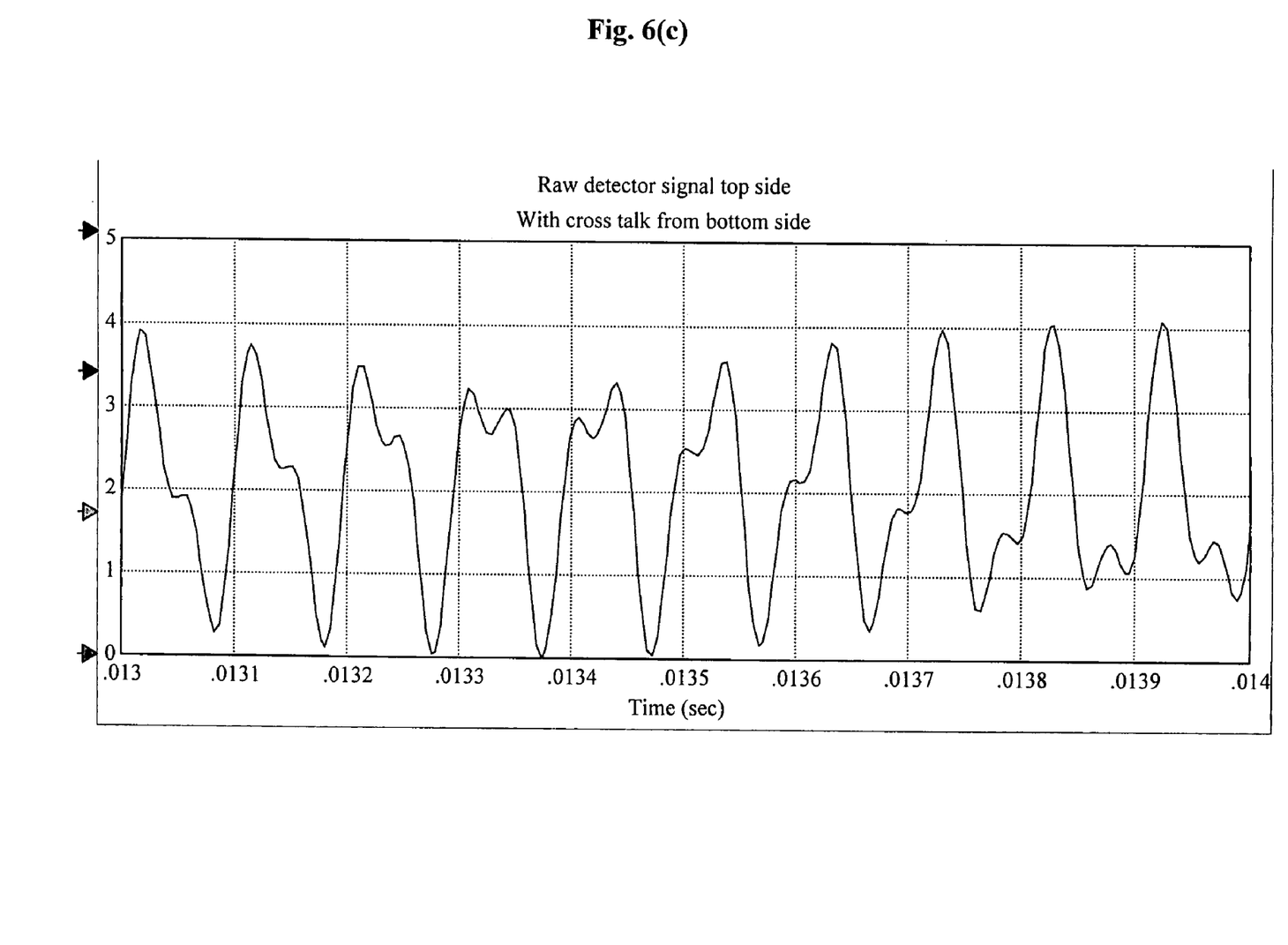

FIGS. 6(a), (b) and (c) shows examples of wave forms for the upper and lower sensor 30, 32. The two upper graphs in FIGS. 6(a) and (b) show the measuring on a fully opaque sheet that has no cross talk between the sensors. The oscillator frequency in this simulation is 10.000 kHz for upper head 30 and 20.400 kHz for lower head 32, or a ratio of 2.04:1. The resulting detected signals in each head are in this case sinusoidal and at different frequencies. The third graph in FIG. 6(c) shows the resulting wave form on top side measurement detector 30g with 30% signal cross talk contributed from bottom source modulation. It is the task of the synchronous demodulation of the present invention to unravel this complex wave form and by doing so eliminate the un-desired cross talk component.

Figure 7A:
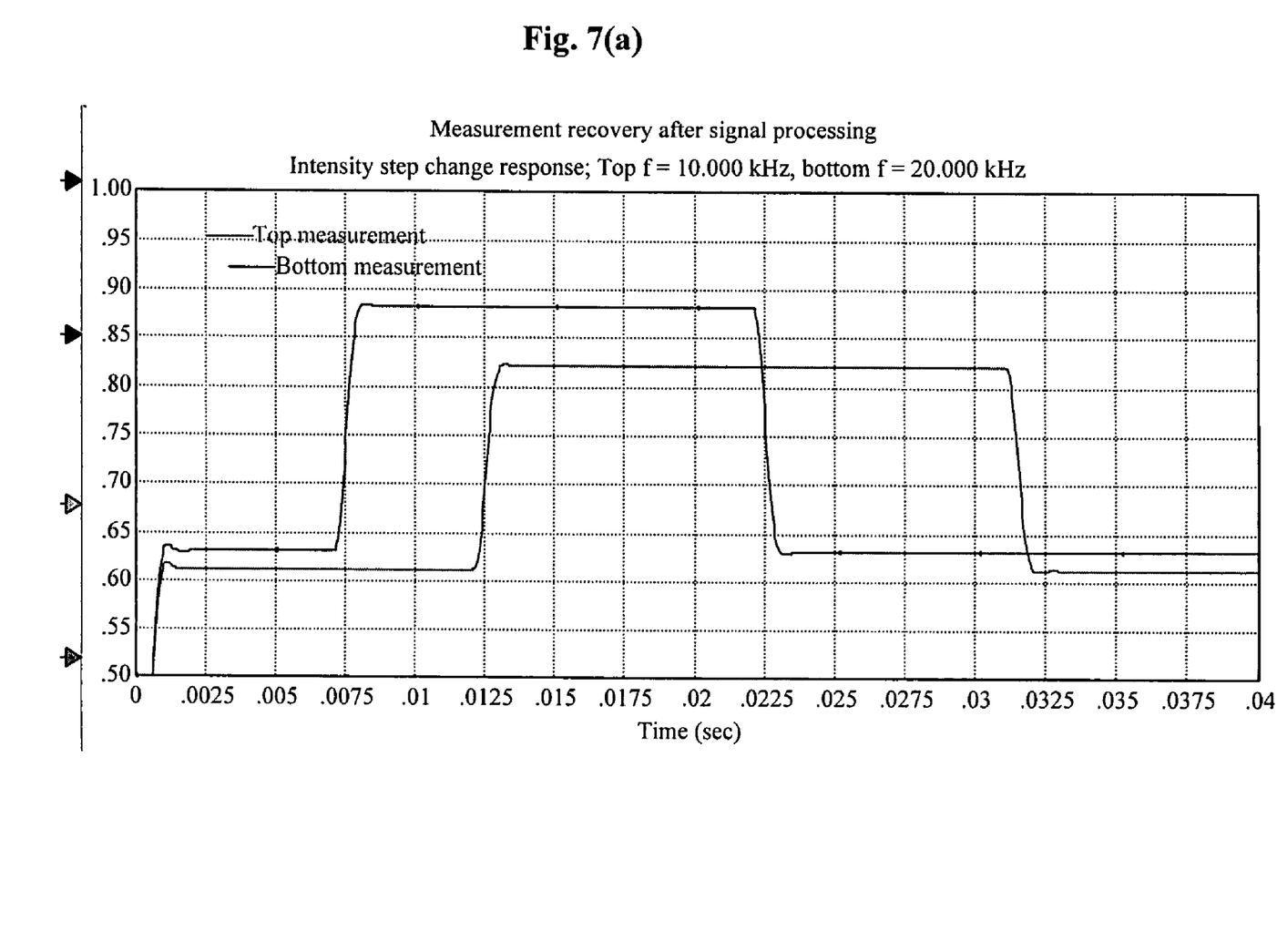
FIGS. 7(a), (b) and (c) show the resulting sensor signal output of the complete processing chain shown in FIG. 5.
Figure 7B:
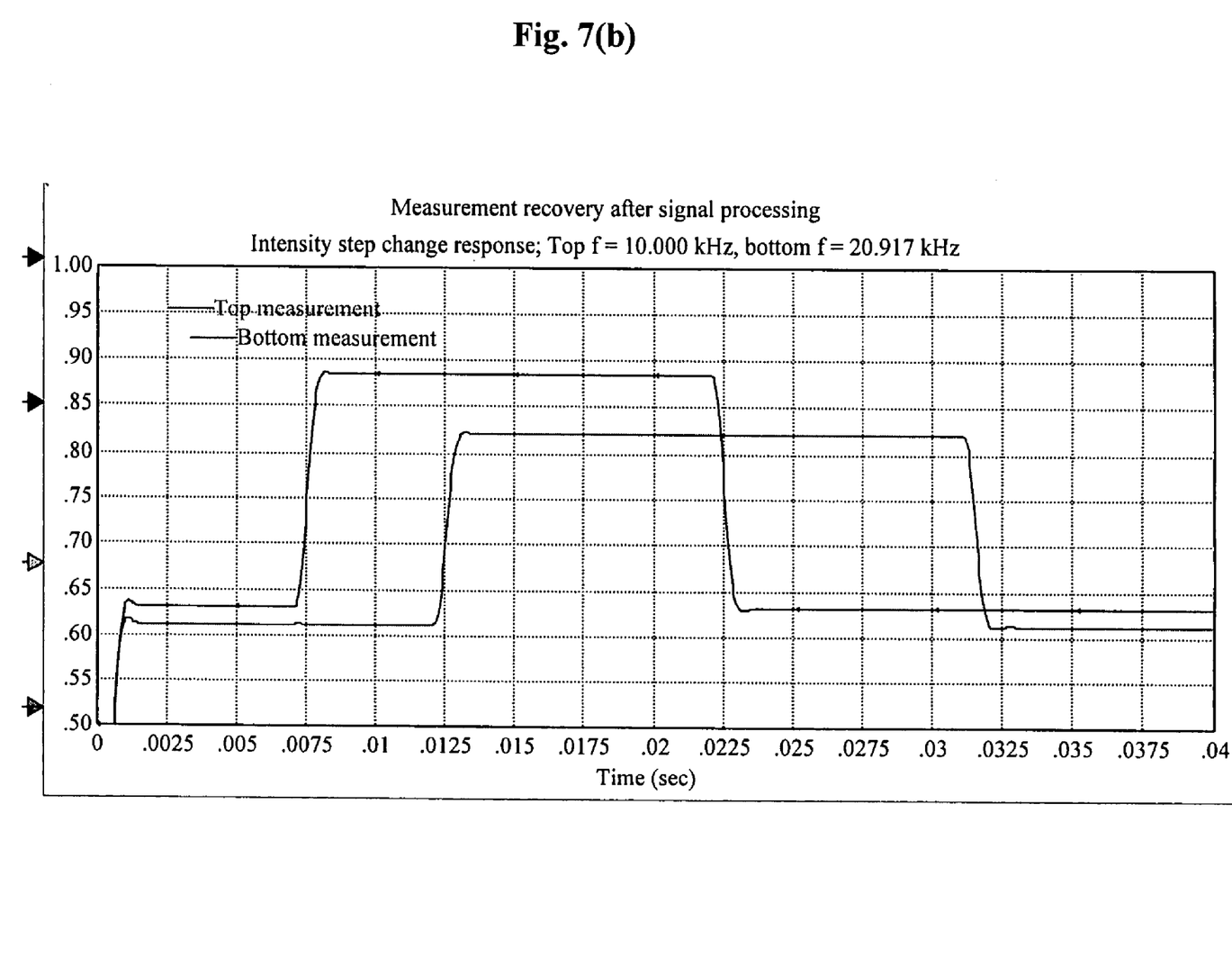
Figure 7C:
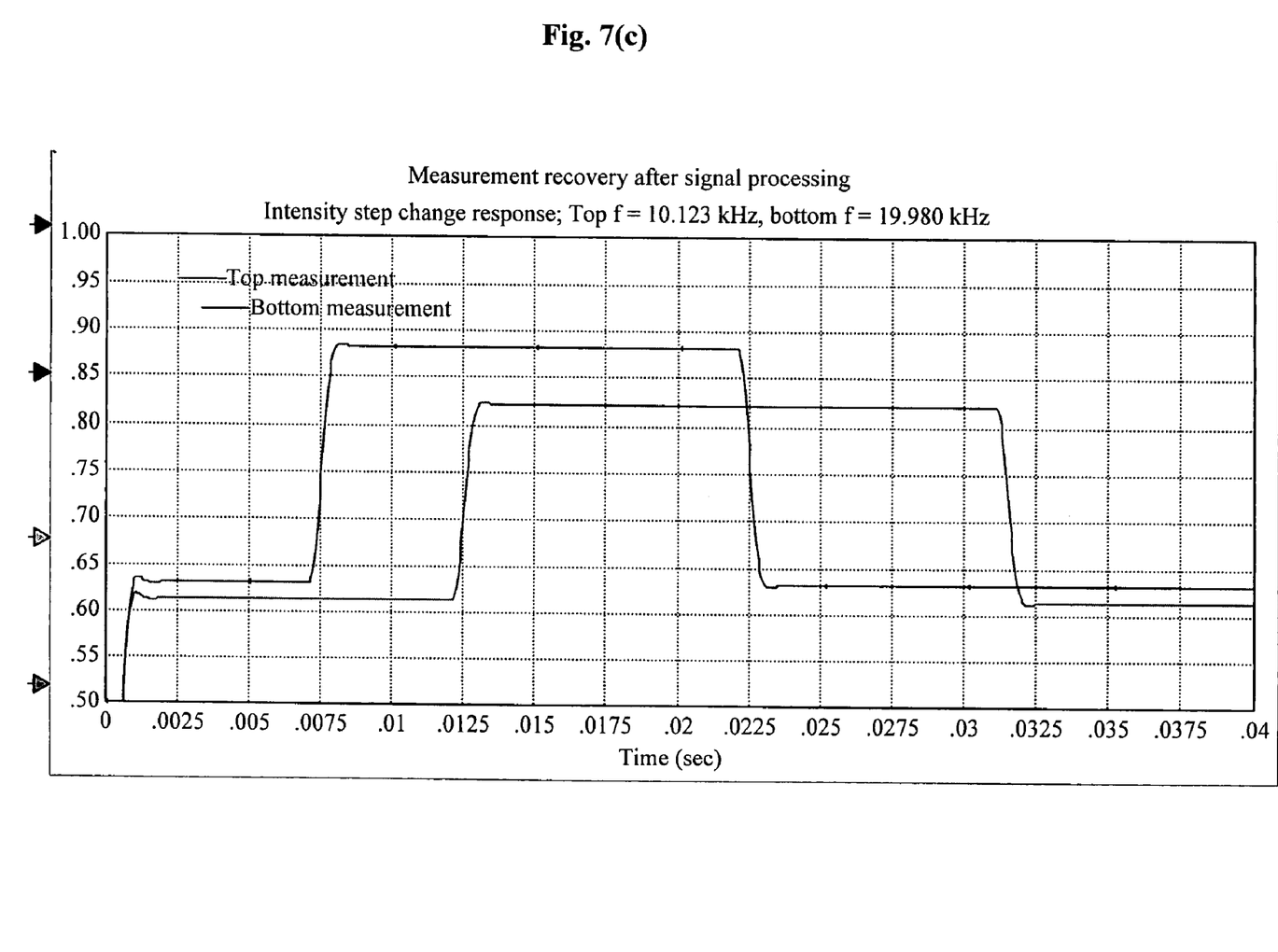

FIGS. 7(a), (b) and (c) show the resulting sensor signal output of the complete signal processing chain as illustrated in FIG. 5, and with 30% of the raw measurement signals on each side originating from cross talk from the opposing side source. In this simulation, the source intensity on each side is furthermore independently changed by major steps up and down. The resulting processed measurement signals on each side are independent of the intensity changes on the opposing side, thus demonstrating very low cross talk after the specified signal processing.

In FIGS. 7(a), (b) and (c), the same step changes and cross talk conditions are furthermore repeated at three slightly different modulation frequency pairs for the upper and lower heads. The frequency pairs thus exemplified are randomly chosen at (1) 10.000/20.000 kHz for FIG. 7(a), (2) 10.000/20.917 kHz for FIG. 7(b) and (3) 10.123/19.980 kHz for FIG. 7(c). Other simulations give similar results. As evident from the results, there is no need for exact frequency tracking or phase lock between the top and bottom sensor heads 30, 32 and a frequency tolerance of approximately ±5% is sufficient.

Figure 8:
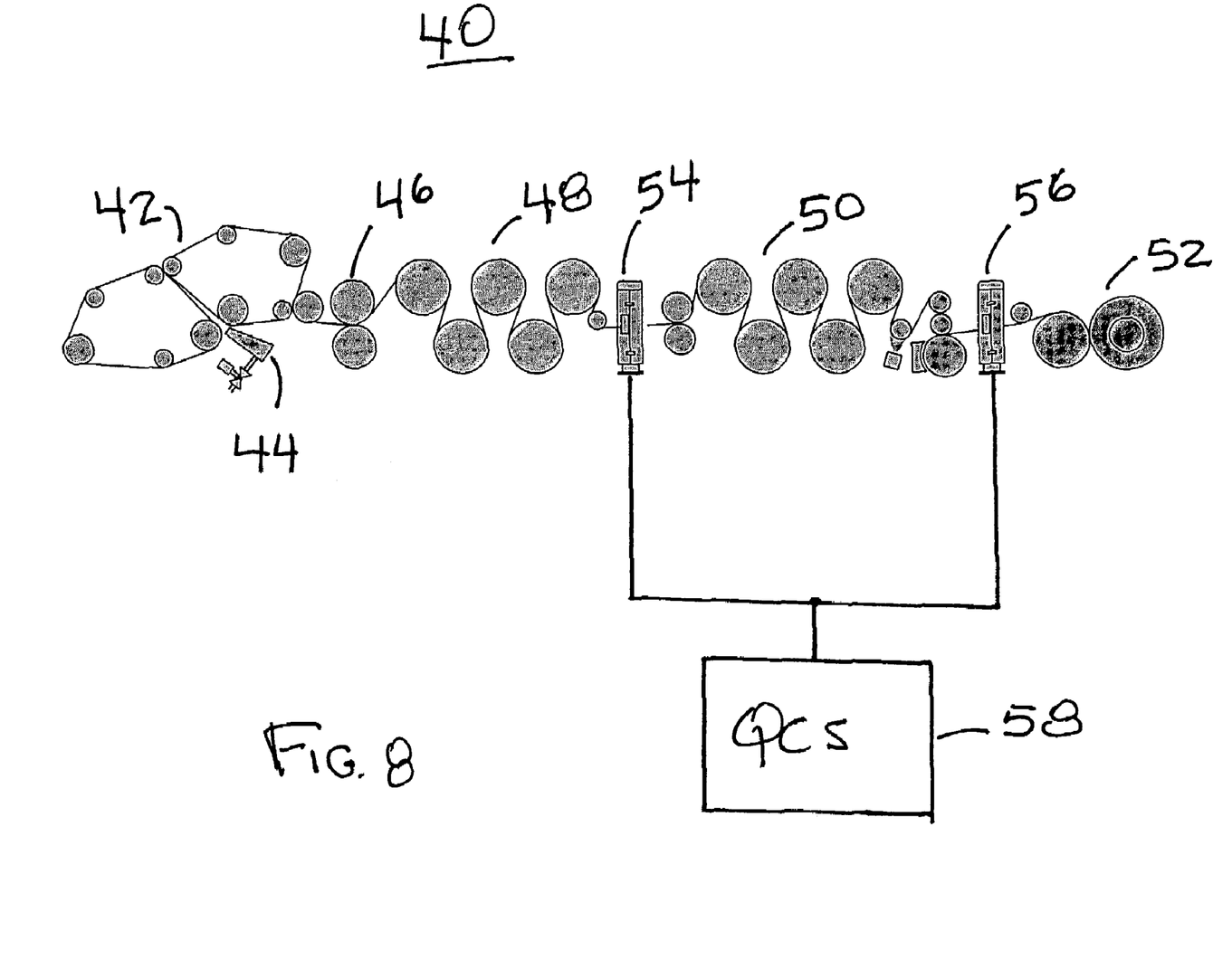
FIG. 8 shows an example of a sheet making system including a paper making machine and quality control system that can be used with the sensor of the present invention.

Referring now to FIG. 8, there is shown in simplified form a typical system for making a sheet such as paper that includes a papermaking machine 40 that can use the sensor 30, 32 of the present invention. Machine 40 includes a forming section 42 that has a headbox 44. As is well known to those of ordinary skill in the papermaking art, in the modern production of paper a continuous fiber/water slurry is formed as a moving web. The slurry is in the headbox 44 and is deposited from the headbox 44 through a long horizontal slit onto a perforated web or wire.

As the slurry moves down the machine 40 the water is removed first at pressing section 46 and then at a first dryer section 48 and a second section dryer 50 to leave the fiber which forms the paper web. The paper web is wound on reel 52.

As is shown in FIG. 8, machine 40 includes a first scanning or non scanning frame 54 mounted across the machine between dryer sections 48 and 50. Examples of a scanning measurement can be found in U.S. Pat. No. 5,479,720 entitled "Method And Apparatus For Measuring Web Thickness And Other Characteristics Of A Moving Web" the disclosure of which is hereby incorporated herein by reference. The frame has an opening through which the moving paper web moves. Frame 54 includes one or more sheet property sensors, such as the sensor of the present invention, that, when frame 54 is a scanning frame, scan back and forth across the moving web to each measure one or more properties of the moving web. Machine 40 also includes a second scanning or non-scanning frame 56 mounted across the machine between dryer section 50 and reel 52. Frame 56 includes one or more sensors, such as the sensor of the present invention, that, when frame 56 is a scanning frame, scan back and forth across the moving sheet to each measure one or more properties of the moving web. The paper machine 40 may be a complete process as illustrated in FIG. 8, or a sub-process involving only certain manufacturing steps, for instance surface treatment to an previously already produced paper web to achieve a higher gloss paper.

As is shown in FIG. 8, the papermaking system also includes a quality control system (QCS) 58 in the form of a computing device that interfaces with the output of the sensors mounted on frames 54 and 56 and contains software that uses the outputs from the sensors to control the machine 40 in order to obtain on the reel 52 a paper web having predetermined desired properties. As is well known to those of ordinary skill in the papermaking art, QCS 58 is connected to all of the equipment in a papermaking system that provides either measurements of the process or can be controlled to affect the properties of the moving web. However, for ease of illustration the QCS 58 is shown in FIG. 8 as only connected to frames 54 and 56.

It should be appreciated that the sensor of the present invention, provided it has means of modulating the energy in a controlled fashion and preferably at a high rate, can be used to measure several different properties of a moving sheet such as gloss, brightness, smoothness, texture, color, coat weight, crepe, surface moisture and non-contacting caliper and may use several different types of energy such as UV, visible light, infrared, radio frequency, microwave, broadband, or X-ray in making that measurement.

It is to be understood that the description of the foregoing exemplary embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A method for measuring properties of a moving web in which sensor heads, each comprising at least one source for providing energy and an associated detector system for detecting energy reflected from said web to be measured, are installed on both of sides of said web to measure the same location on said web, wherein each detector system comprises a measurement detector, a reference detector, a synchronous detector and a phase detector, said method comprising:

providing from said at least one source on one side of said web energy modulated at a first frequency;

simultaneously providing from said at least one source on the other side of said web energy modulated at a second frequency which is different than said first frequency;

using said detector system on said one side of said web to detect only energy reflected from said web modulated at said first frequency; and using said detector system on said other side of said web to detect only energy reflected from said web modulated at said second frequency; and wherein the steps of using the detector systems to detect energy reflected from the web each comprise using the phase detector to detect zero crossings of a signal from the reference detector and using the synchronous detector to detect energy reflected from the web using zero crossings and a signal from the measurement detector.

2. An apparatus for measuring properties of a moving web comprising:
first and second sensor heads for installation on opposite sides of said web to measure the same location on said web, each of said first and second sensor heads comprising at least one source for providing energy and at least one associated detector for detecting energy reflected from said web; and
said at least one source of said first sensor head providing energy modulated at said first frequency and said at least one source of said second sensor head providing energy modulated at said second frequency which is different than said first frequency;
said at least one detector of said first sensor head detects only energy reflected from said web modulated at a first frequency and said at least one detector of said second sensor head detects only energy reflected from said web modulated at a second frequency; and
wherein each of the first and second sensor heads comprises a measurement detector, a reference detector, a synchronous detector and a phase detector for detecting zero crossings of a signal from the reference detector, the synchronous detector using the zero crossings and a signal from the measurement detector to detect energy associated with a particular frequency, the particular frequency being the first frequency in the first sensor head and the particular frequency being the second frequency in the second sensor head.

3. The apparatus of claim 2 wherein said energy provided from said at least one source of said first sensor head and said second sensor head are both selected from a group consisting of: UV, visible light, infrared, radio frequency, microwave, broadband, or X-ray.

4. The apparatus of claim 2 wherein said first frequency is about two times said second frequency.

5. The apparatus of claim 2 further comprising a first source of a signal having said first frequency and a second source of a signal having said second frequency.

6. The apparatus of claim 2 wherein said signal having said first frequency and said signal having said second frequency are each selected to have a low level of second harmonic content.

7. The apparatus of claim 5 further comprising synchronous demodulators for selectively detecting only the energy associated with said first frequency in said first sensor head and said second frequency in said second head.

8. The apparatus of claim 2 further comprising a frame in which said first and second sensor heads are mounted in a manner such that when said frame straddles said moving web said sensor heads are on opposite sides of said moving web and measure a property of said moving web at the same location on said moving web.

9. The apparatus of claim 8 wherein said frame is selected from a group consisting of: a scanning frame or a non-scanning frame.

10. The apparatus of claim 8 wherein said first and second sensor heads measure one or more of the properties of said web selected from a group consisting of: gloss, brightness, smoothness, texture, color, coat weight, crepe, surface moisture, non-contacting caliper or sheet flatness.

11. The apparatus of claim 9 further comprising a quality control system connected to at least said first and second sensor heads.

12. A system for measuring properties of a moving web comprising:
a machine for making said moving web, said machine comprising one or more frames mounted on said machine such that each of said one or more frames straddles said moving web;
one or more quality control systems for controlling one or more properties of said moving web; and
one or more sensors mounted on at least one of said one or more frames, each of said one or more sensors comprising:
first and second sensor heads mounted on said at least one of said one or more frames such that said heads are on opposite sides of said web to measure the same location on said web, each of said first and second sensor heads comprising at least one source for providing energy and at least one associated detector for detecting energy reflected from said web; and
said at least one source of said first sensor head providing energy modulated at said first frequency and said at least one source of said second sensor head providing energy modulated at said second frequency which is different than said first frequency;
said at least one detector of said first sensor head detects only energy reflected from said web modulated at a first frequency and said at least one detector of said second sensor head detects only energy reflected from said web modulated at a second frequency; and
wherein each of the first and second sensor heads comprises a measurement detector, a reference detector, a synchronous detector and a phase detector for detecting zero crossings of a signal from the reference detector, the synchronous detector using the zero crossings and a signal from the measurement detector to detect energy associated with a particular frequency, the particular frequency being the first frequency in the first sensor head and the particular frequency being the second frequency in the second sensor head.

13. The system of claim 12 wherein said energy provided from said at least one source of said first sensor head and said second sensor head are both selected from a group consisting of: UV, visible light, infrared, radio frequency, microwave, broadband, or X-ray.

14. The system of claim 12 wherein said first frequency is about two times said second frequency.

15. The system of claim 12 wherein each of said one or more sensors further comprise a first source of a signal having said first frequency and a second source of a signal having said second frequency.

16. The system of claim 12 wherein said signal having said first frequency and said signal having said second frequency are each selected to have a low level of second harmonic content.

17. The system of claim 15 wherein each of said one or more sensors further comprise synchronous demodulators for selectively detecting only the energy associated with said first frequency in said first sensor head and said second frequency in said second head.

18. The system of claim 12 wherein each of said one or more frames are selected from a group consisting of: a scanning frame or a non-scanning frame.

* * * * *

UNITED STATES PATENT AND TRADEMARK OFFICE
CERTIFICATE OF CORRECTION

PATENT NO. : 7,593,106 B2  Page 1 of 1
APPLICATION NO. : 11/439653
DATED : September 22, 2009
INVENTOR(S) : Ake Arvid Hellstrom It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this

Twenty-first Day of September, 2010

David J. Kappos
*Director of the United States Patent and Trademark Office*